United States Patent
Blessing et al.

(10) Patent No.: US 11,185,451 B2
(45) Date of Patent: Nov. 30, 2021

(54) INDIRECT PRINTING OF AGM

(71) Applicant: The Procter & Gamble Company, Cincinnati, OH (US)

(72) Inventors: Horst Blessing, Cincinnati, OH (US); Hans Adolf Jackels, Mechernich (DE); Siegfried Link, Schleiden (DE); Volker Maier, Cologne (DE); Thomas Ludwig Woschnik, Euskirchen (DE); Martin Geoffrey Scaife, Cologne (DE)

(73) Assignee: The Procter & Gamble Company, Cincinnati, OH (US)

( * ) Notice: Subject to any disclaimer, the term of this patent is extended or adjusted under 35 U.S.C. 154(b) by 835 days.

(21) Appl. No.: 15/699,227

(22) Filed: Sep. 8, 2017

(65) Prior Publication Data
US 2017/0367907 A1    Dec. 28, 2017

Related U.S. Application Data

(63) Continuation of application No. 14/247,350, filed on Apr. 8, 2014, now Pat. No. 9,782,307, which is a
(Continued)

(30) Foreign Application Priority Data

Jul. 28, 2004   (EP) ..................... 04017789

(51) Int. Cl.
*A61F 13/535*    (2006.01)
*A61F 13/15*     (2006.01)
(Continued)

(52) U.S. Cl.
CPC ...... *A61F 13/535* (2013.01); *A61F 13/15634* (2013.01); *A61F 13/15658* (2013.01);
(Continued)

(58) Field of Classification Search
CPC ...... A61F 13/00991; A61F 2013/15821; A61F 13/5323; A61F 13/535
See application file for complete search history.

(56) References Cited

U.S. PATENT DOCUMENTS 4,571,924 A * 2/1986 Bahrani ............... B65B 29/028
                                                    53/453
4,666,647 A * 5/1987 Enloe ................ A61F 13/15658
                                                    19/148
(Continued)

FOREIGN PATENT DOCUMENTS

EP    0 203 289 A2    12/1986
EP    1 088 537 B1     3/2010
(Continued)

OTHER PUBLICATIONS

European Search Report, dated Sep. 9, 2005, 2 pages.
(Continued)

*Primary Examiner* — Philip C Tucker
*Assistant Examiner* — John Blades
(74) *Attorney, Agent, or Firm* — Sarah M. DeCristofaro; Wednesday G. Shpp

(57) ABSTRACT

The present invention relates to a method of applying absorbent gelling material (AGM) granules by indirect printing onto an carrier layer for use in an absorbent article, particularly diaper for babies or adults, training pants, pull-up diapers (diaper pants), sanitary napkins, panty liners or the like. These articles typically comprise the carrier layer with the AGM particles together with further layers, making up the complete article.

9 Claims, 9 Drawing Sheets

Related U.S. Application Data continuation of application No. 12/899,114, filed on Oct. 6, 2010, now Pat. No. 8,735,645, which is a continuation of application No. 11/183,357, filed on Jul. 18, 2005, now Pat. No. 7,838,722.

(51) Int. Cl.

| | | |
|---|---|---|
| *A61F 13/532* | (2006.01) | |
| *B05C 1/08* | (2006.01) | |
| *B05C 19/04* | (2006.01) | |
| *G06F 30/20* | (2020.01) | |
| *B32B 37/00* | (2006.01) | |
| *A61F 13/514* | (2006.01) | |
| *A61F 13/53* | (2006.01) | |
| *B05C 11/10* | (2006.01) | |

(52) U.S. Cl.
CPC .. *A61F 13/15764* (2013.01); *A61F 13/15804* (2013.01); *A61F 13/51476* (2013.01); *A61F 13/5323* (2013.01); *B05C 1/0804* (2013.01); *B05C 1/0808* (2013.01); *B05C 1/0817* (2013.01); *B05C 19/04* (2013.01); *B32B 37/00* (2013.01); *G06F 30/20* (2020.01); *A61F 2013/15821* (2013.01); *A61F 2013/53051* (2013.01); *A61F 2013/530481* (2013.01); *B05C 11/1039* (2013.01); *B32B 2250/03* (2013.01); *B32B 2307/726* (2013.01); *B32B 2555/02* (2013.01); *Y10T 156/10* (2015.01); *Y10T 156/1002* (2015.01); *Y10T 156/1007* (2015.01); *Y10T 156/1023* (2015.01); *Y10T 156/1025* (2015.01); *Y10T 428/24628* (2015.01)

(56) References Cited

U.S. PATENT DOCUMENTS

| | | | |
|---|---|---|---|
| 4,927,685 A | 5/1990 | Marshall et al. | |
| 4,994,053 A | 2/1991 | Lang | |
| 5,030,314 A | 7/1991 | Lang | |
| 5,030,814 A | 7/1991 | Tange et al. | |
| 5,128,082 A | 7/1992 | Makoui | |
| 5,562,646 A | 10/1996 | Goldman et al. | |
| 5,628,845 A | 5/1997 | Murray et al. | |
| 5,762,712 A | 6/1998 | Sohn | |
| 5,766,388 A | 6/1998 | Pelley et al. | |
| 5,830,202 A | 11/1998 | Bogdanski et al. | |
| 6,048,489 A | 4/2000 | Reiter et al. | |
| 6,093,474 A | 7/2000 | Sironi | |
| 6,730,387 B2 | 5/2004 | Rezai et al. | |
| 6,982,052 B2 * | 1/2006 | Daniels | A61F 13/15203 264/101 |
| 7,838,722 B2 | 11/2010 | Blessing et al. | |
| 8,735,645 B2 | 5/2014 | Blessing et al. | |
| 2003/0201052 A1 | 10/2003 | Koslow | |
| 2006/0024433 A1 | 2/2006 | Blessing et al. | |
| 2006/0048880 A1 * | 3/2006 | Blessing | A61F 13/15634 156/60 |
| 2009/0056867 A1 | 3/2009 | Moriura et al. | |
| 2011/0017398 A1 | 1/2011 | Blessing et al. | |
| 2014/0220241 A1 | 8/2014 | Blessing et al. | |

FOREIGN PATENT DOCUMENTS

| | | |
|---|---|---|
| JP | 2693814 B2 | 12/1997 |
| JP | 11-320742 A | 11/1999 |
| JP | 2000-107221 A | 4/2000 |
| JP | 2000238161 A | 9/2000 |
| JP | 2003-165173 A | 6/2003 |
| WO | WO-1993/002861 A1 | 2/1993 |
| WO | WO-1995/016420 A1 | 6/1995 |
| WO | WO-1996/007380 A1 | 3/1996 |

OTHER PUBLICATIONS

International Search Report, dated Jul. 20, 2011, 5 pages.
All Office Actions; U.S. Appl. No. 11/183,357.
All Office Actions; U.S. Appl. No. 12/899,114.
All Office Actions; U.S. Appl. No. 14/247,350.
Extended EP Search Report and Written Opinion for 10154324, dated Jul. 20, 2011, 5 pages.
Extended EP Search Report and Written Opinion for 10151628.4, dated Jan. 21, 2011; 6 pages.
Third Party Opposition for Application Serial No. 04017789.1 dated Jan. 13, 2011, 11 pgs.
PCT Search Report and Written Opinion for PCT/US2005/026238 dated Dec. 8, 2005, 12 pages.

* cited by examiner

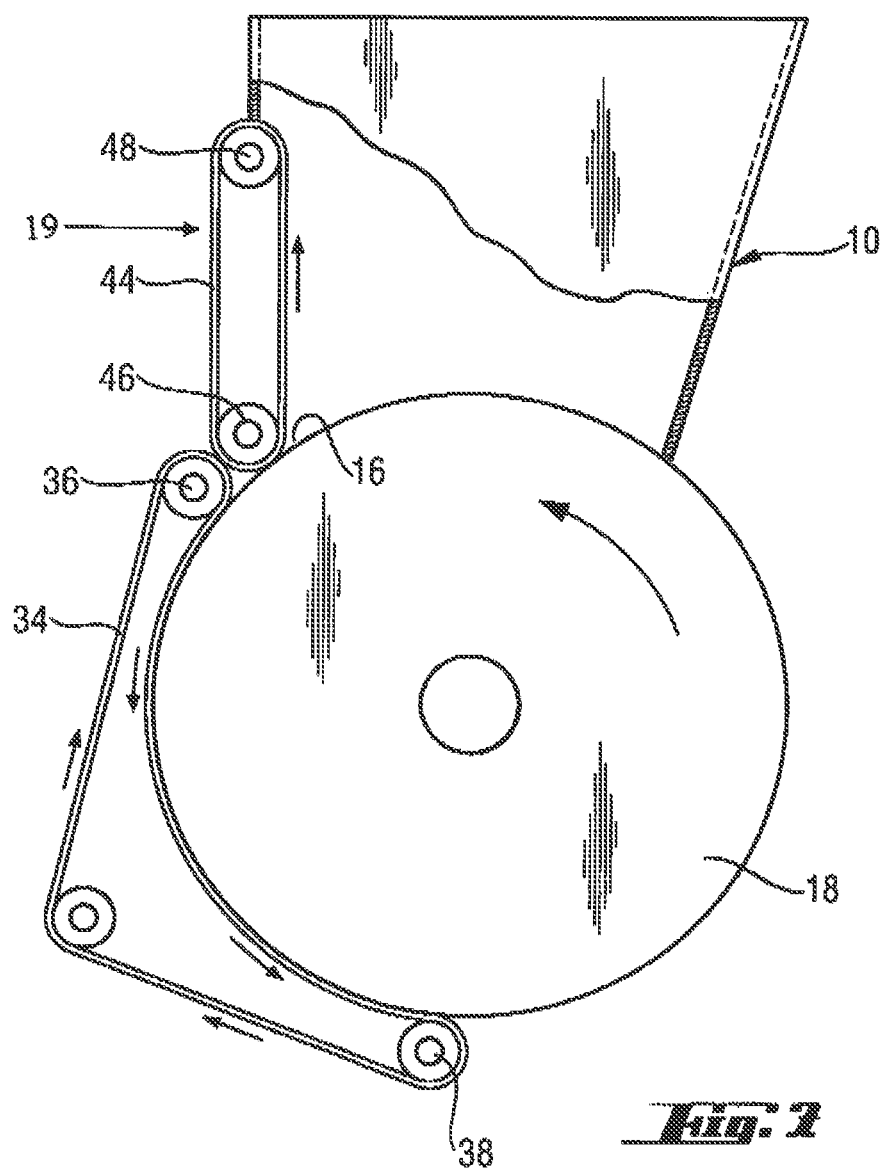

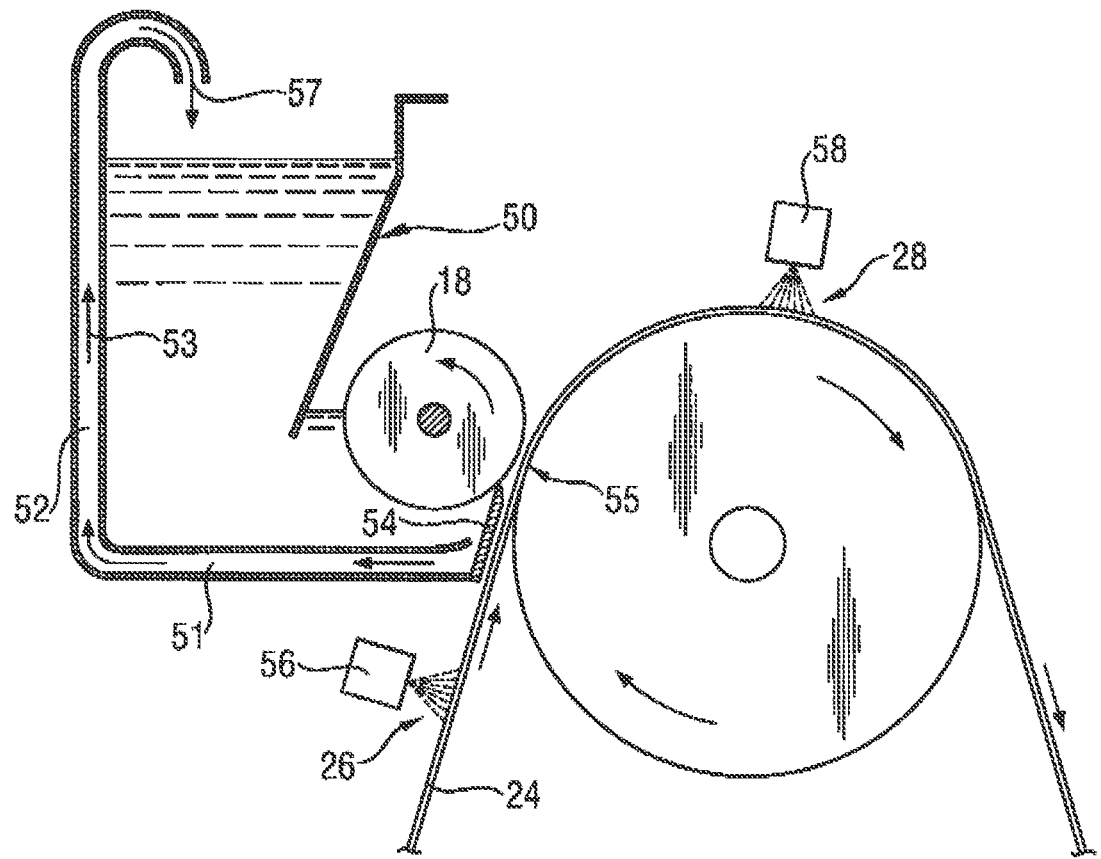

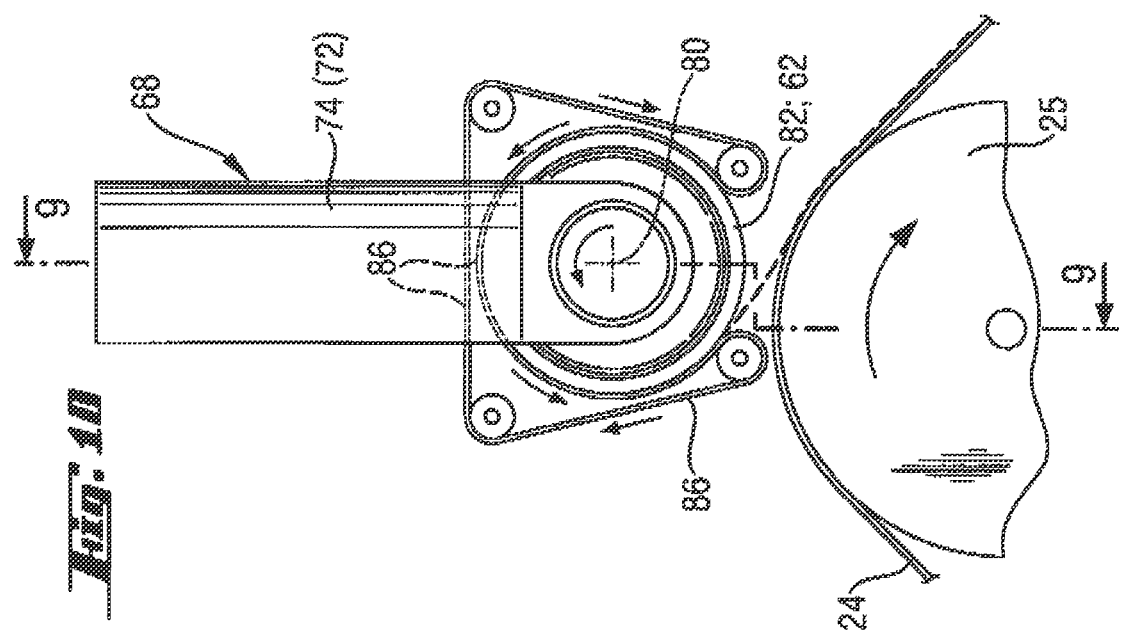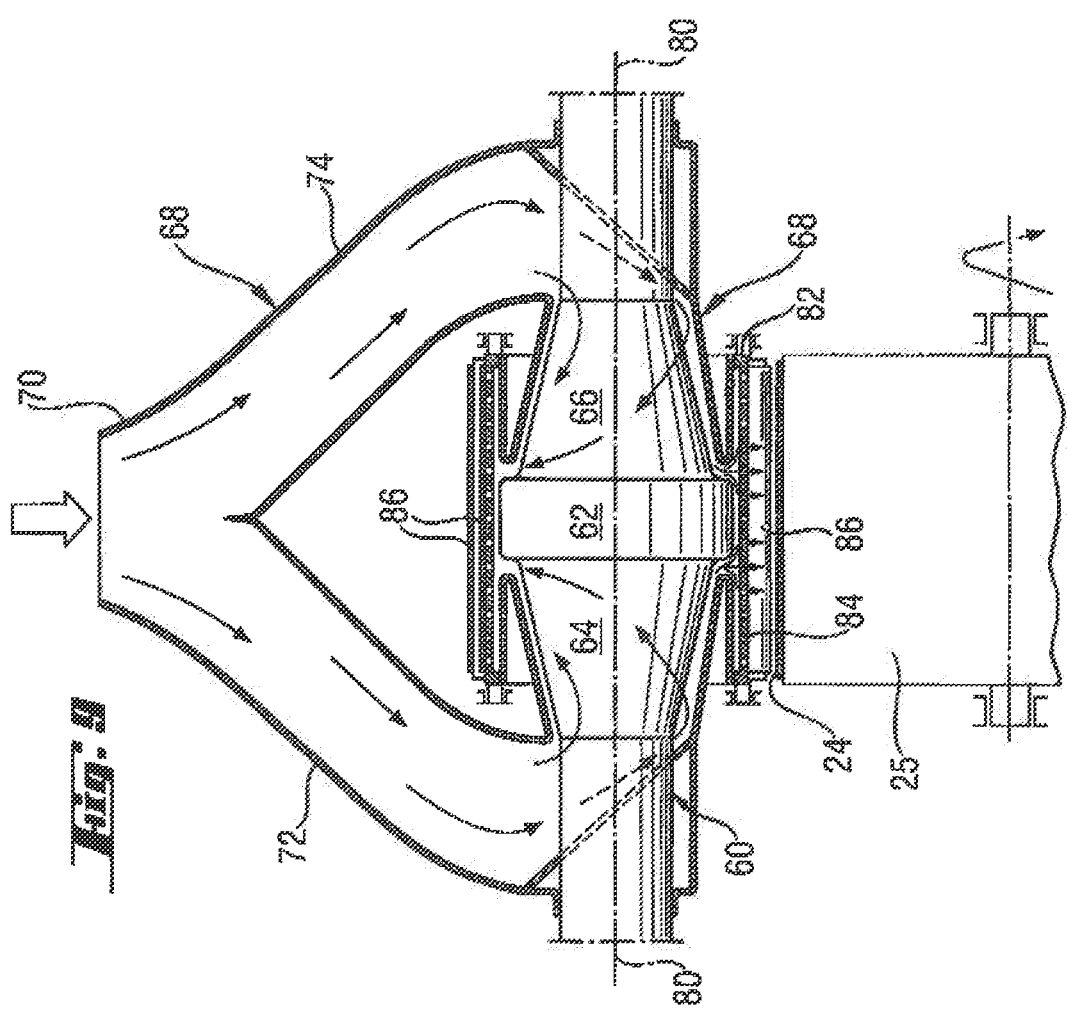

INDIRECT PRINTING OF AGM

FIELD OF THE INVENTION

The present invention relates to a method of applying absorbent gelling material (AGM) granules onto an carrier layer for use in an absorbent article, particularly diaper for babies or adults, training pants, pull-up diapers (diaper pants), sanitary napkins, panty liners or the like. These articles typically comprise the carrier layer with the AGM particles deposited thereon by indirect printing together with further layers making up the complete article.

BACKGROUND OF THE INVENTION

The term "AGM granules" as used herein includes materials capable of absorbing and storing a high amount of liquid compared with the volume thereof. "AGM" is the abbreviation of Absorbent Gelling Materials. These materials are mainly formed by superabsorbent polymers. In the present context the AGM material may be used as granules of different particle size including powder like materials or a mixture of powder material and granules of different particle size or forms (e. g. fibers).

AGM materials of this kind are usually embedded into absorbent pads of melt blown fibers or cellulose fibers (or similar fibrous materials and combinations thereof) or directly deposited onto a non-woven carrier layer. The present invention is applicable to both of these methods. This kind of "absorbent article" may be used for example for manufacturing a diaper, a sanitary towel or even a liquid gathering article of any kind.

Various approaches have been proposed for obtaining AGM granule distribution on a substrate having a predetermined pattern and thickness profile. These approaches include blowing an airborne mixture of AGM granules and fibers through a conduit onto a vacuum drum. Methods of this kind only allow a limited control of the pattern and the distribution of the thickness of the AGM over the surface onto which the AGM is distributed.

Particularly in case of low or no cellulose fiber containing absorbent cores, having AGM granules as the only liquid storage material, AGM granule distribution with accuracy with respect to shape and discreetness is highly important.

In this context it should be mentioned that it is possible to use single or multi piece cores, one layer of AGM or several layers on top of each other overlapping or besides each other. This also allows to use different AGM's in different layers. Thus the possibilities of variation of the achieved product are nearly endless. However, high accuracy of the granule distribution is important.

SUMMARY OF THE INVENTION

Thus the present invention is directed to a method for applying AGM granules onto a surface with high accuracy of the distribution, pattern and the amount of AGM material on the surface by indirect printing. Such a process method can be used in an application of AGM particles requiring accurate, print like positioning of granules or powders on a carrier layer. One particular application may be the making of primarily AGM/glue comprising cores for disposable diapers or parts of such cores.

According to a first embodiment of the present invention, the indirect printing method according to the invention is characterized in that the AGM granules are taken up by a transfer device from a bulk storage of AGM granules, said transfer device having recesses on the surface thereof, the number, size and position of which determining the amount and pattern of AGM granules taken up by the transfer device, the transfer device being moveable from the bulk storage to a position passed by the carrier layer (transfer or meeting position), means being provided for retaining the AGM granules inside said recesses during movement of the transfer device to said meeting (or transfer) position, and means being provided for expelling said AGM granules onto the carrier layer in said transfer position.

The invention further refers to an apparatus, particularly an apparatus for conducting the method according to the invention.

In the following indirect printing shall mean the transfer of AGM which is separated from the bulk storage of AGM before it is in contact with the carrier layer. Direct printing means that the AGM is not separated from the bulk storage of AGM before it is in contact with the carrier layer. This is not included in the present invention.

The present invention provides a method and apparatus which significantly increases AGM deposition accuracy. The standard deviation achieved so far has been reduced to about ¼ of what has been achieved with advanced prior technology. Thus diaper cores having an accurate distribution profile of AGM in the lateral and the longitudinal direction can be obtained. The method according to the invention allows especially deposition of AGM granules on fast moving carrier layers at surface speeds of 1 m/sec up to 3 m/sec, preferably up to 5 m/sec, or even 10 m/sec and even more preferably up to 15 m/sec with high accuracy. Because of the accuracy of the deposition of AGM granules, the invention allows manufacturing of e. g. an absorbent core without cellulose or similarly absorbent and/or hydrophilic fibers in diapers which results in extreme core thinness and improved comfort and fit in use for the articles.

The term "transfer device" as used herein includes any moveable member being capable of taking up AGM granules in a predetermined shape and a thickness profile and depositing the granules-without amending the configuration thereof-on a carrier substrate.

A preferred embodiment of the transfer device is a patterned rotary drum or roll, which is called "printing roll" or "transfer roll" in the present context because the transfer of a pattern of AGM granules can be comparable with printing. Another embodiment would be a moveable belt having recesses on the surface and being moved between the AGM granule bulk storage and the transfer position.

The term "bulk" or "bulk storage" of AGM granules refer in the present context to any kind of supply of granules, particularly a hopper.

"Retaining means" are provided to keep the AGM granules taken up by the recesses of the transfer device in these recesses during movement from the bulk to the transfer position where the granules are delivered to the carrier layer. In one preferred embodiment the retaining means is a belt, which is guided along the surface of the transfer device, particularly the printing roll, on the way from the bulk to the transfer position. Other possible embodiments, which are particularly preferred are vacuum means for keeping the AGM granules in the recesses. Also the use of an electrostatic field is possible "Expelling means" in the present context means delivering the AGM granules in the transfer position as defined above to a carrier substrate. For delivering the granules, the granules may be expelled by air jets or an electrostatic field or just by gravity.

BRIEF DESCRIPTION OF THE DRAWINGS

The above and further features, aspects and advantages of the present invention will become better understood with regard to the following description making reference to the accompanying drawings.

FIG. 5 again corresponds to FIG. 2 with a modification of one feature;

FIG. 7 shows an embodiment being a combination of FIGS. 3 and 6;

FIG. 8 shows another embodiment of an apparatus according to the invention and for conducting the methods according to the invention;

FIG. 10 is a front view from the left side in FIG. 9.

DETAILED DESCRIPTION OF THE INVENTION

Figure 1:
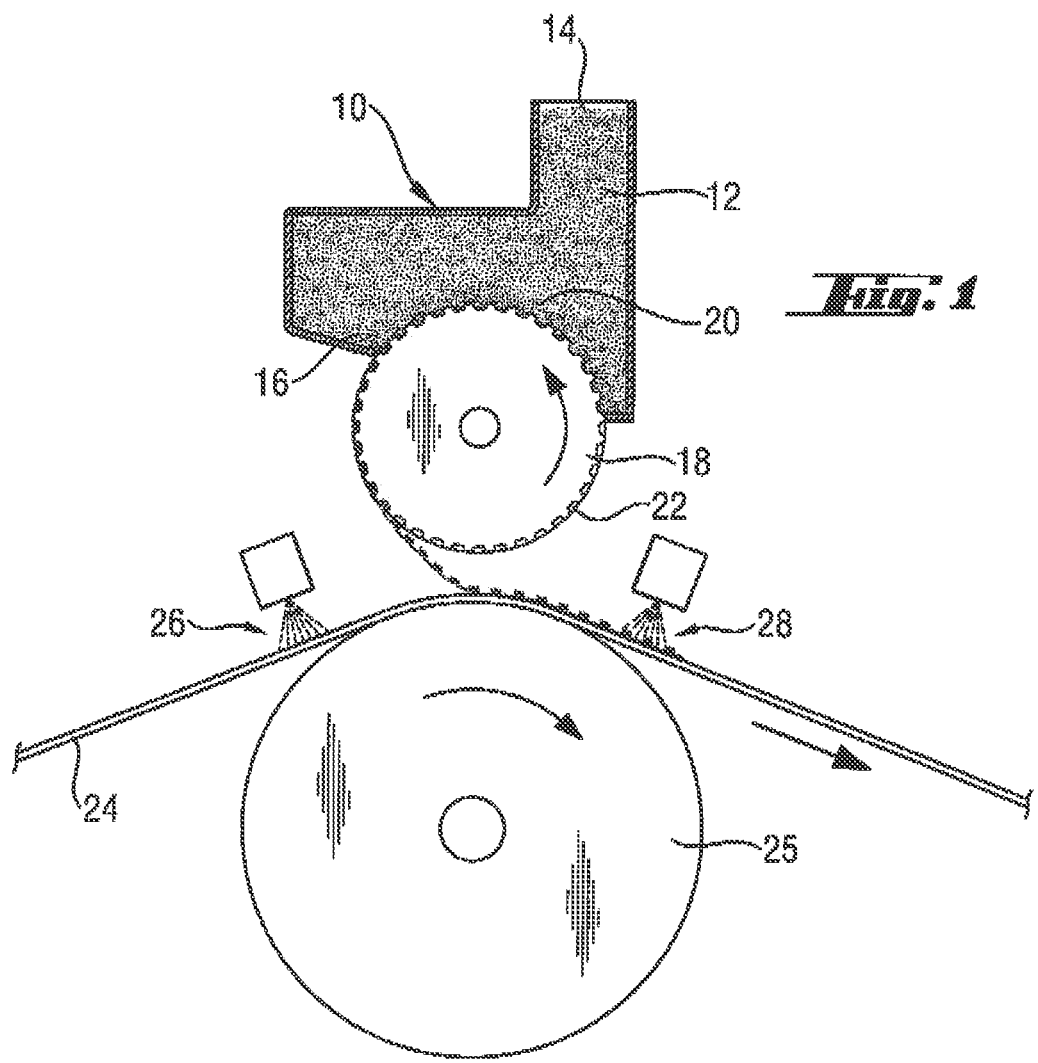
FIG. 1 illustrates one embodiment of the present invention.

FIG. 1 shows a hopper (10) filled with a bulk of AGM material (12). The hopper (10) has a supply opening (14) on the upper side and a delivery opening (16) at the bottom. The hopper forms one embodiment of what is called "bulk" in the present context.

A printing roll (18) enters into the opening (16) in the hopper (10) in a way that the bottom of the hopper surrounding the opening (16) closely follows the contour of the roller (18) and an unintended drop out of AGM granules is prevented.

The printing roll (18) is provided with holes or recesses (22) on the surface thereof which are filled with AGM granules from the lower end (20) of the bulk of AGM material (12) in the hopper (10), while the surface of the roll (18) passes through the AGM material (12) inside the hopper (10). The number, the size and the position of the recesses (22) are selected such that the volume and the pattern of the recesses correspond to the intended pattern and thickness profile of the AGM material which is to be received by the printing roll and to be transferred to a carrier layer as will be explained below.

The printing roll (18) forms one embodiment of a transfer device according to the present invention. Another embodiment could for instance be formed by a belt having recesses in the surface thereof for receiving AGM material.

A rotatable printing roll however may be a preferred embodiment.

The AGM granules are taken up by the recesses (22) of the printing roll (18) when one of the recesses (22) on the transfer roll (18) is in this loading position. The AGM granules are retained in these recesses on the way from the hopper (10) to a position called "transfer or meeting position" herein where the printing roll (18) which is rotated in counter clockwise direction in FIG. 1 is in a position immediately opposite the surface of a carrier layer (24). The carrier layer (24) is supported by a rotating support roll (25).

The carrier layer is for instance a non-woven web onto which the AGM granules are expelled or laid down (by gravity) from the printing roll. For holding the AGM granules on the carrier layer (24), glue is preferably sprayed onto the carrier layer (24) upstream the transfer position between the printing roll (18) and the carrier layer (24), which upstream position is designated by reference numeral (26). Because the glue is applied in this upstream position (26) onto the carrier layer (24), the AGM granules are retained on the carrier layer (24). A particularly preferred glue for retaining the AGM granules on the carrier layer (24) is a micro fiber glue with very thin fiber made by spraying a hot melt adhesive material through respectively thin nozzles. Such nozzles are commercially available from Nordson Company, Dawsonville, Ga., USA.

It is preferred that the support roll (25), which could alternatively also be provided by a moving belt, is also holding the AGM particles down onto the carrier, especially by use of a pressure differential (vacuum) through a screen forming the cylindrical surface of the support roll (25). In another position downstream the transfer position between the printing roll (18) and the carrier layer (24), which position is designated by (28), glue is—preferably but optional—sprayed onto the AGM granules on the carrier layer (24), which glue preferably is also a microfilament glue entering like fibers between the granules of the AGM to hold the whole deposit together. In an alternative embodiment it is also possible to apply a cover layer carrying glue onto the AGM granules.

When large amounts of glue are applied at positions (26) and/or (28) it is advantageous to use materials for the cylindrical support roll surface, which have a low or no tendency to accumulate adhesive residue. This can be Teflon™ coated surfaces or if a belt instead of a support roll is used, silicon rubber materials. Especially in case the carrier layer (24) is exposed to a vacuum on the inside of the support roll the surface of the support roll can be made of a silicon rubber screen (preferably metal reinforced).

As shown in FIG. 1, in this particular embodiment the printing roll (18) is moving through the AGM material by rotation of the roll in the counterclockwise direction designated by the arrow in FIG. 1, AGM granules are taken up in the recesses (22) of the roll, but there is of course a certain risk that additional AGM granules beyond those filling the recesses are carried out of the hopper between the surface of the printing roll (18) and adjacent edge of the bottom of the hopper. Therefore, scraping means (19) are provided at this edge one example of which is shown in FIG. 2.

Figure 2:
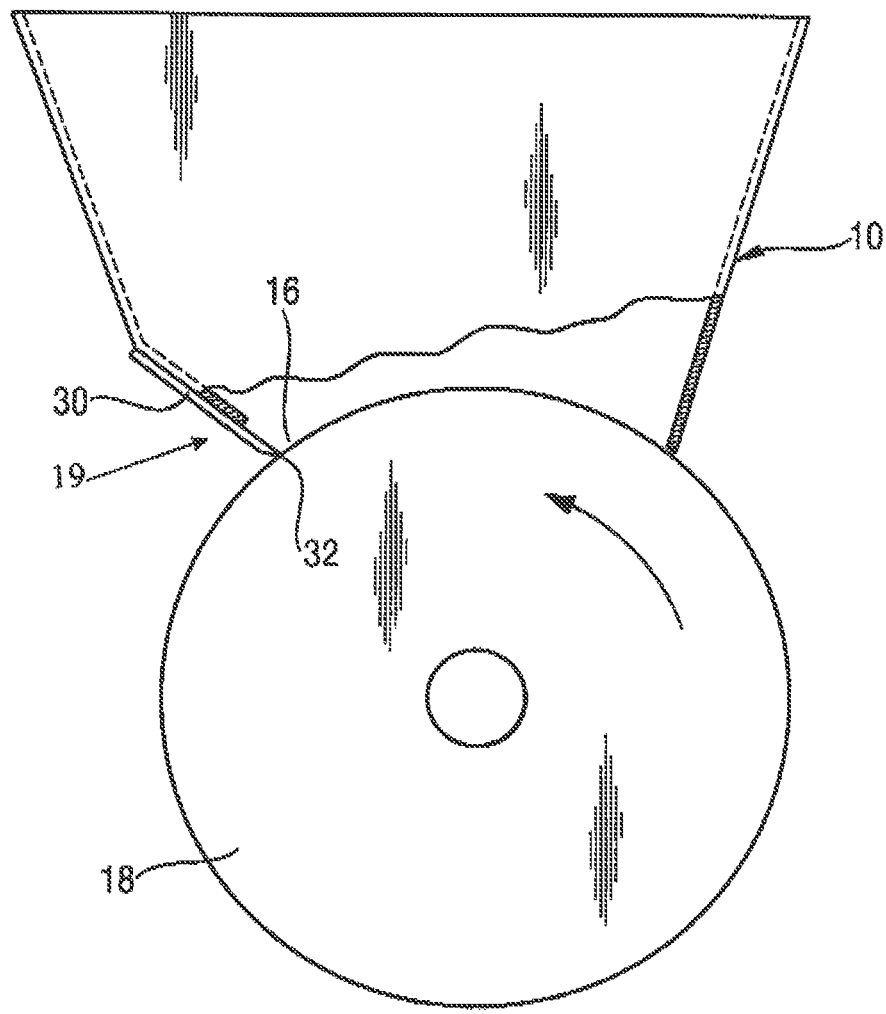
FIG. 2 is a diagrammatic illustration of the embodiment of FIG. 1 showing an additional detail.

In FIG. 2 those members or elements which have been already described in connection with FIG. 1, are designated by the same reference numerals.

The scraping means (19) in FIG. 2 are formed by a doctor blade (30) having a scraping edge (32) being in close contact with the surface of the printing roll (18). The distance between the doctor blade (30) and the printing roll (18) should be above 0 mm to prevent excess pressures and damage to the equipment and the AGM particles. The particle size mix is one of the factors to consider when selecting the scraping blade distance. E.g. very large AGM particles with mean diameter of 900 micrometer and above would need a spacing of less than 900 micrometer. The upper useful spacing limit should be about 1 mm with the preferred spacing between 0.01 and 0.5 mm, more preferably between 0.03 and 0.1 mm to ensure good scraping at extended production runs.

Figure 3:
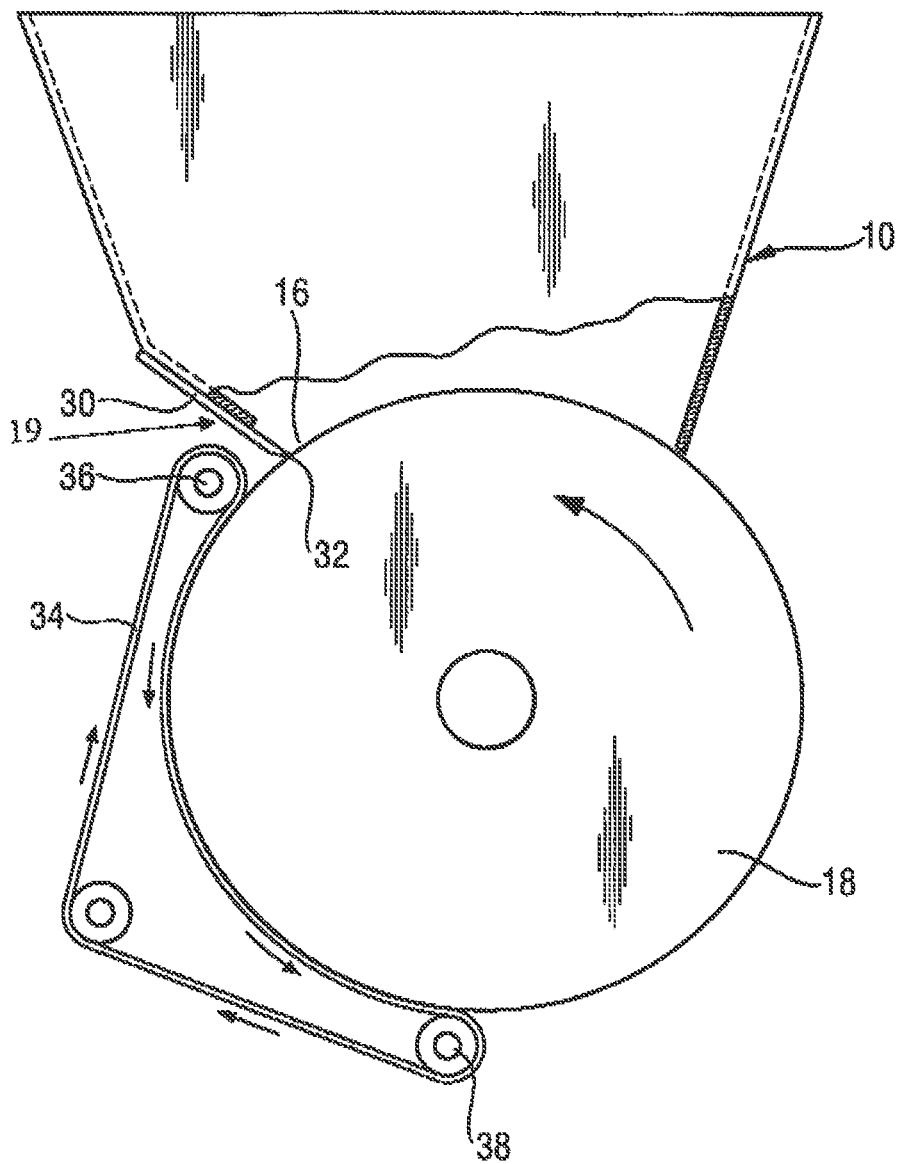
FIG. 3 illustrates a modification of the embodiment of FIG. 2.

FIG. 3 illustrates an embodiment corresponding to the embodiment of FIG. 2 but additionally showing retaining means for retaining the AGM granules in the recesses (not shown) provided in the surface of the printing roll (18) on the way from the hopper (10) to the transfer position.

One possibility to hold the AGM granules in the recesses may be a vacuum applied to the inner side of the printing roll (18) in combination with suction holes (not shown) in the bottom of the recesses. Another embodiment of retaining means as shown in FIG. 3 is formed by an endless belt (34) which is moved together with the rotation of the printing roll (18) along with the surface thereof from a position immediately downstream the doctor blade to a position immediately upstream the transfer position where the granules are transferred to the carrier layer (24) not shown in FIG. 3. The belt is driven around an upper and a lower guide roll (36,38) in the upper and lower position of the path of the belt adjacent the printing roll (18) and around a third guide roll spaced from the surface of the printing roll and forming a triangle with the other guide roll (36,38). The belt (34) may be driven by driving one of these three rolls to move the belt (34) in the direction marked by arrows. Alternatively, the belt may be idling and moved by contact with the surface of the printing roll (18).

Figure 4:
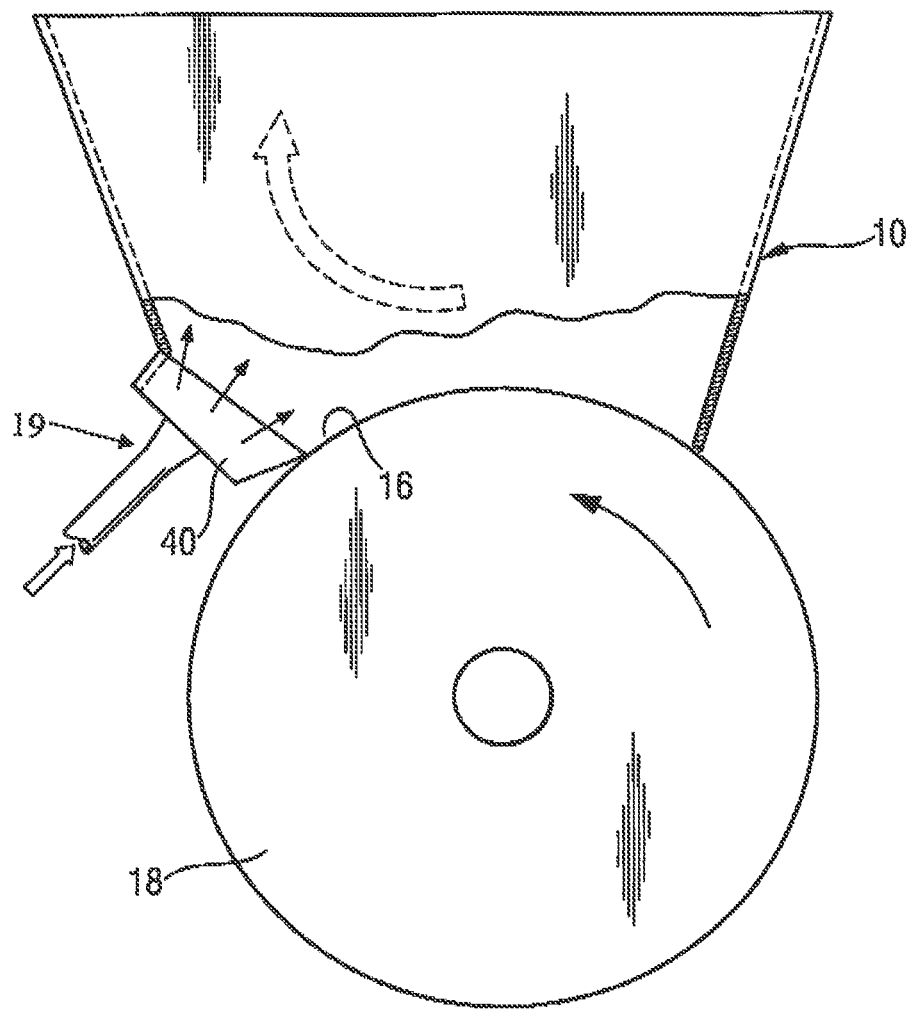
FIG. 4 corresponds to FIG. 2 with a modification of one feature.

FIG. 4 shows an alternative embodiment of the scraping means (19) of FIGS. 2 and 3. The reference numerals of FIGS. 2 and 3 are also used in FIG. 4 for corresponding parts. Instead of the doctor blade of FIGS. 2 and 3, the embodiment of FIG. 4 is provided with an air jet box (40) arranged in the position of the doctor blade (30) of FIGS. 2 and 3 and ejecting air under pressure opposite to the moving direction of the surface of the printing roll (18), as shown in FIG. 4, to keep the AGM granules back from the gap between the air jet box and the surface of the printing roll 18.

The embodiment of FIG. 5 which again basically corresponds to the foregoing embodiments of FIGS. 2 to 4 shows another modification of the scraping means (19) which in this case are formed by a rotatable brush (42) in the position of the doctor blade mentioned before to keep the AGM granules back from leaving the hopper 10 by rotation in counter clockwise direction.

FIG. 6 again shows another embodiment of the scraping means (19), which in this case is formed by a moveable belt running around a lower and an upper guide roll (46,48) one of which may be driven by a suitable drive not shown. The belt (44) moves on the side of the AGM materials substantially vertically upward as shown by the arrow and returns down on the outer side of the hopper (10).

The belt (44) lifts the AGM material on the inner side of the hopper (10) to keep the AGM material away from leaving the hopper through the gap between the surface of the printing roll and the belt (44).

Figure 6:
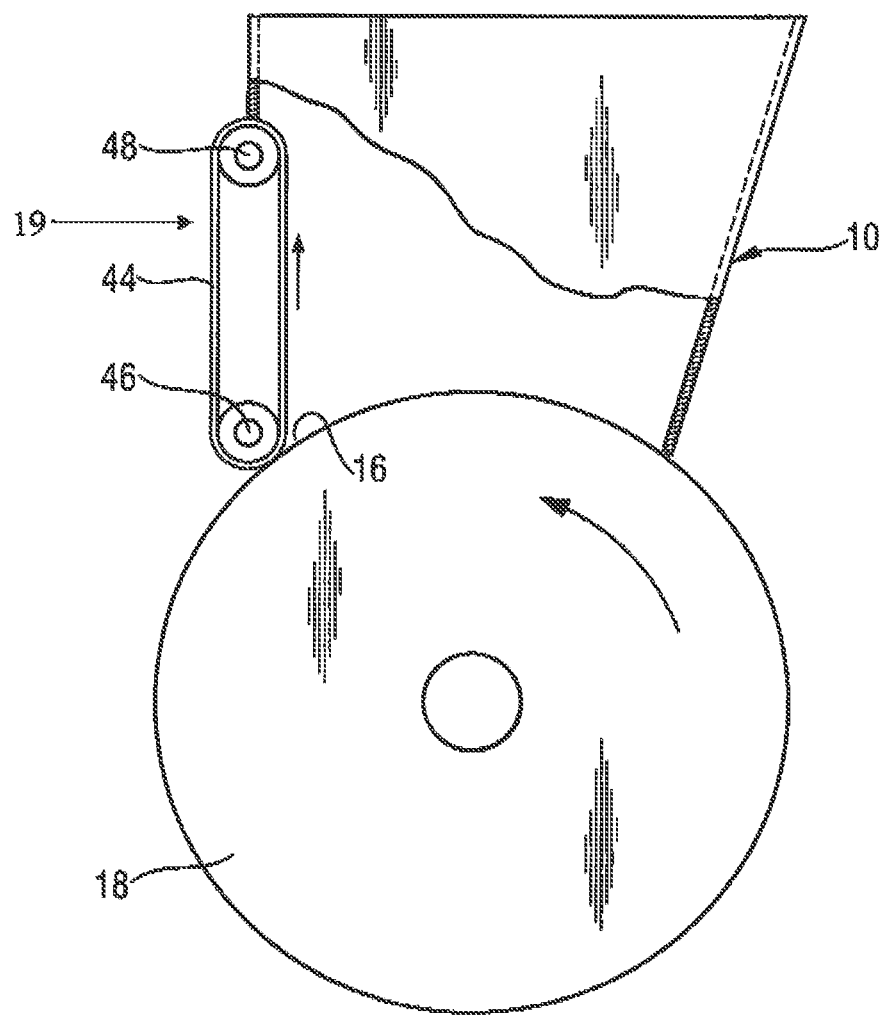
FIG. 6 again corresponds to FIG. 2 with a modification of one feature.

FIG. 7 shows an embodiment which is substantially a combination of the embodiments of FIGS. 3 and 6, comprising a belt (34) for retaining the AGM granules in the recesses of the printing roll and another belt (44) with the function of scraping means as discussed in connection with FIG. 6.

FIG. 8 shows an embodiment the hopper (50) of which is formed as a fluidized bed for keeping the AGM granules in a floating state. The printing roll designated by (18) in this case rotates through the fluidized granules which are taken up by the recesses in the surface of the printing roll (18). AGM granules extending beyond the recesses or adhering to the surface of the printing roll (18) outside the recesses are stripped away from the printing roll by a doctor blade (54) acting as scraping means and being arranged in a position immediately upstream the meeting position designated by (55) in this case where the printing roll is positioned immediately opposite the carrier layer (24) supported by the lay down drum. In the positions (26,28) upstream and downstream the meeting position there are position glue heads (56,58) for applying glue onto the carrier layer (24) in the position (26) and onto the deposited AGM granules in the position (28) applied onto the carrier layer. In this case, the printing roll immerges into the AGM bulk storage from the top.

In preferred embodiment, the system shown in FIG. 8 further comprises an airborne particle cycling system (51, 52, 57). In this system particles are transported from a location close to the meeting position (55) along conducts (51, 52) in the direction of arrow (53) to a return conduct end (57). In this way the particles are prevented from being stuck or settling in the region of meeting position (55) due to agitation reduction in that region of the fluidized bed. The particle cycling system usually can be operated by an air current in the pipe transporting the particles along the conducts.

Figure 9:
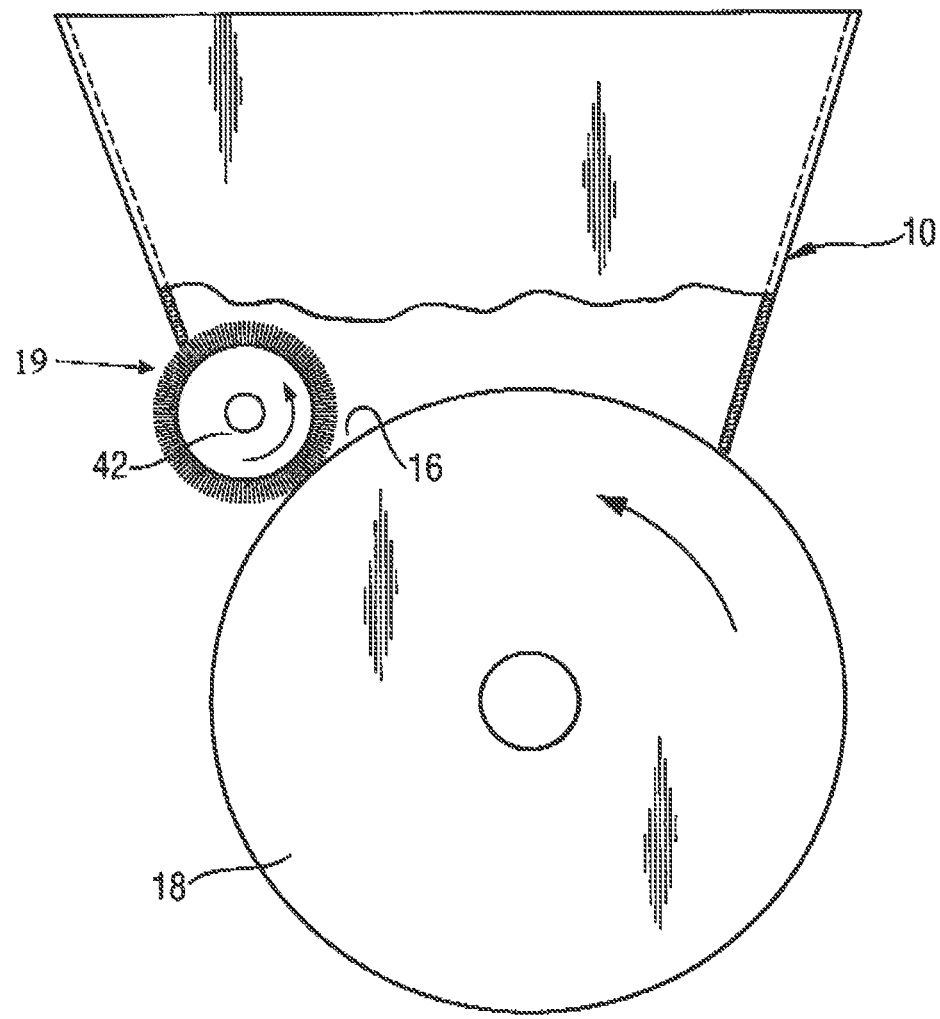
FIG. 9 is a cross section along line 9-9 of another embodiment of the invention shown in FIG. 10.

In FIG. 9, there is shown an indirect particle printing station comprising an AGM supply (70, 72, 74) connected to a stator housing (68), centrifugal roll (60) having its axis (80) along a horizontal line from left to right in FIG. 9. FIG. 9 is a cross section view along line 9 in FIG. 10, which is showing a side view of the particle printing station of FIG. 9. In FIG. 10 the carrier onto which AGM is deposited is shown on a transport cylinder also referred to a support roll (25, partially shown). The centrifugal roll (60) comprises a central portion (62) of cylindrical form and two frustoconical inlet portions (64, 66) on both sides thereof in axial direction. The inlet portions (64, 66) are connected with an AGM supply system (68) formed by a supply tube (70) divided in two branch tubes (72, 74) which are connected with the inlet portions (64, 66) of the centrifugal roll (60) at their axial ends. Thus AGM is supplied through the supply tube (70) into the branch tubes (72, 74) and transported in the inlet portions (64, 66) by centrifugal forces and finally into the central portion (62) of the centrifugal roll. At this position the AGM leaves the centrifugal roll and the stator (68) and, still by centrifugally created pressure is pressed against the inside of the screen printing roll (82) which is partially covered on the outside with a belt (86).

This printing roll is provided with openings (not shown) in the circumferential wall forming a pattern of suitable shape and size through which, at each rotation of the centrifugal roll, AGM granules leave the printing station and are deposited without contact on a carrier layer (24) (as shown in FIG. 10).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for indirectly applying absorbent gelling material granules onto a carrier layer, said method comprising:
    providing a fluidized bed comprising said absorbent gelling material granules in a floating state;
    rotating a print roll having a plurality of recesses through the fluidized bed, such that said absorbent gelling material granules are taken up by the recesses;
    providing an airborne particle cycling system to transport particles from a region upstream of a meeting position of said print roll and said carrier layer along conducts to a return conduct end facing said fluidized bed;
    applying a glue onto said carrier layer upstream of said meeting position of said print roll and said carrier layer; and
    after applying said glue, depositing said absorbent gelling material granules on said carrier layer at said meeting position of said print roll and said carrier layer without contact of said print roll and said carrier layer.

2. The method of claim 1, wherein said carrier layer comprises a non-woven carrier layer.

3. The method of claim 1, further comprising stripping absorbent gelling material granules in excess of an amount required to fill a volume of said recesses from the print roll.

4. The method of claim 1, wherein said carrier layer is supported by a rotating drum.

5. The method of claim 1, wherein said carrier layer is supported on a moving belt.

6. The method of claim 1, further comprising applying a second glue onto said absorbent gelling material granules deposited onto said carrier layer downstream of said meeting position.

7. The method of claim 1, further comprising applying a cover layer onto said absorbent gelling material granules downstream of said meeting position.

8. The method of claim 7, wherein said cover layer comprises a second glue.

9. The method of claim 1, further comprising expelling said absorbent gelling material granules onto said carrier layer at the meeting position.

* * * * *